United States Patent [19]
Yamamoto et al.

[11] Patent Number: 5,623,340
[45] Date of Patent: Apr. 22, 1997

[54] FOREIGN PARTICLE INSPECTION APPARATUS

[75] Inventors: Kenji Yamamoto, Kawasaki; Fuminori Hayano, Tokyo; Tsuneyuki Hagiwara, Kawasaki; Hideyuki Tashiro, Yokohama, all of Japan

[73] Assignee: Nikon Corporation, Tokyo, Japan

[21] Appl. No.: 391,602

[22] Filed: Feb. 21, 1995

[30] Foreign Application Priority Data

Feb. 22, 1994 [JP] Japan .................................... 6-023997

[51] Int. Cl.$^6$ ................................................ G01N 21/88
[52] U.S. Cl. ............................................................. 356/237
[58] Field of Search .............................. 356/237; 437/8, 437/939

[56] References Cited

U.S. PATENT DOCUMENTS

| | | | |
|---|---|---|---|
| 4,468,120 | 8/1984 | Tanimoto et al. | 356/237 |
| 5,164,603 | 11/1992 | Hartman et al. | 356/237 |
| 5,274,434 | 12/1993 | Morioka et al. | 356/237 |
| 5,463,459 | 10/1995 | Morioka et al. | 356/237 |

*Primary Examiner*—Richard A. Rosenberger
*Attorney, Agent, or Firm*—Shapiro and Shapiro

[57] ABSTRACT

A foreign particle inspection apparatus, for detecting a foreign particle on a reticle or the like includes an illumination system for irradiating an inspection area on a specimen with inspecting light, and plural light-receiving systems adapted to condense the scattered light from a foreign particle in the inspection area and having respective light-receiving areas on the specimen, each smaller than the inspection area. Each of the light-receiving areas of the plural light-receiving systems overlaps partially with at least one of the other light-receiving areas. The plural light-receiving systems are so arranged that any point in the inspection area is covered by the light-receiving areas of at least two of the plural light-receiving systems. A foreign particle in the inspection area is detected by a detection system, based on the lights condensed by the plural light receiving systems.

22 Claims, 8 Drawing Sheets

FOREIGN PARTICLE INSPECTION APPARATUS

BACKGROUND OF THE INVENTION

1. Field of the Invention

The present invention relates to a foreign particle inspection apparatus, adapted for detecting a foreign particle deposited on the surface for example of a mask, a reticle or a glass plate (such as glass substrate for liquid crystal display device) to be used in an exposure apparatus for producing a semiconductor device, a liquid crystal display device or the like.

2. Related Background Art

If an exposing mask or reticle (hereinafter collectively called reticle), to be used in the photolithographic manufacture of a semiconductor device or the like, has a surfacial defect such as a foreign particle, there will result a loss in the production yield of the manufactured semiconductor devices. For avoiding such loss, the surface of the reticle has been inspected with a foreign particle inspection apparatus, prior to the exposure operation. Also for avoiding the deposition of such a foreign particle directly on the pattern bearing face or the rear face of the reticle, a dust-preventing film, called a pellicle, may be applied on the reticle. Since such a pellicle is displaced or offset from the pattern bearing face of the reticle, conjugate with the exposed face of the photosensitive substrate (such as wafer), a foreign particle of a given size has less influence when deposited on such pellicle than when directly deposited on the reticle. However, the foreign particle present even on the pellicle affects the result of exposure when it exceeds a certain limit, so the surface of such pellicle and the rear face thereof (facing the reticle) are also inspected for the defect such as a foreign particle, by the foreign particle inspection apparatus. In the following description, the reticle will be explained as the object of inspection, but it will be understood that a reticle bearing a pellicle thereon is also included.

FIG. 16 shows an example of the conventional foreign particle inspection apparatus, wherein a reticle 1 is placed on a stage 2 which is movable in the Y-direction by a drive unit 3. The amount of movement of the stage 2 in the Y-direction is constantly measured by a length measuring device 4 such as a linear encoder, and a position signal S1, indicating the measured value of the length measuring device 4 is supplied to a signal processing unit 5. On the other hand, a light beam L1, emitted from an unillustrated light source (such as a laser light source), is reflected and deflected by a galvano scanning mirror 6 (or a polygon scanning mirror) driven by a drive unit 7, and formed by a scanning lens 8 as a light beam L2 converging onto the reticle 1, thereby effecting a scanning operation in the X-direction, along a scanning line 10 between two points 9A and 9B on the reticle 1. The entire surface of the reticle 1 can be scanned with the light beam, by causing the light beam L2 to effect scanning operation in the X-direction and moving the reticle 1 in the Y-direction by the drive unit 3, with a speed lower than that of said scanning operation.

In case the reticle 1 has a surfacial defect such as a foreign particle 11, scattered light L3 is generated by said foreign particle 11 from the light beam L2. The scattered light L3 is respectively condensed by light-receiving lenses $12_1$, $12_2$, $12_3$ onto light-receiving faces of photodetectors $13_1$, $13_2$, $13_3$ such as photomultipliers, which effect photoelectric conversion on the condensed light to respectively provide detection signals $S3_1$, $S3_2$, $S3_3$ to the signal processing unit 5. The three light-receiving optical systems, respectively containing the light-receiving lenses $12_1$–$12_3$, are provided at optimum positions for receiving the light, and are designed to independently receive the light from the entire range of the scanning line 10.

The signal processing unit 5, also receiving a deflection angle signal S2 supplied to the drive unit 7 for the galvano scanning mirror 6, can identify the presence of the foreign particle 11 from the detection signals $S3_1$, $S3_2$ and $S3_3$. In this identification, the foreign particle 11 is identified for example only if all the three detection signals $S3_1$, $S3_2$, $S3_3$ become at least equal to a predetermined level, in order not to misunderstand the diffracted light from the proper circuit pattern on the reticle 1 as the scattered light from the foreign particle.

At the same time, based on the position signal S1 from the length measuring device 4 and the deflection angle signal S2 for the drive unit 7 for the galvano scanning mirror 6, corresponding to the detection of the foreign particle in said three detection signals, the signal processing unit 5 can recognize the position of said foreign particle 11. More specifically the X and Y coordinates of the foreign particle 11 can be respectively identified from the deflection angle signal S2 and the position signal S1.

Also, based on a fact that the scattered light L3 becomes more intense as the foreign particle becomes larger, the signal processing unit 5 identifies the size of the foreign particle 11 from the magnitude of the three detection signals $S3_1$, $S3_2$, $S3_3$. Thus the signal processing unit 5 can display, on a CRT display 14, the coordinates (X, Y) of the foreign particle and the size thereof, for example in the form of a table. Otherwise, simultaneous with the scanning of the reticle 1 with the light beam, the coordinates (X, Y) and size of the detected foreign particle can be displayed on the CRT display 14 in the form of a two-dimensional map.

In such conventional foreign particle inspection apparatus, each of plural light-receiving optical systems, provided in different directions with respect to the scanning line 10, independently receives the light from the entire range of the scanning line 10, and the foreign particle is identified by the photoelectric conversion signals obtained from the light received by said light-receiving optical systems. However, with the recent increase in size of the liquid crystal display device or the like, the reticle to be inspected has become larger and it has become difficult to receive, in each light-receiving optical system, the light from the entire range of the scanning line crossing such large-sized reticle.

Also for such longer scanning line crossing the reticle, the signal processing system becomes complex if plural light-receiving optical systems are arranged along such scanning line and the foreign particle is identified by parallel entry of the photoelectric conversion signals obtained from the lights received by the respective light-receiving optical systems. Also the signal processing system becomes larger in proportion to the number of the light-receiving optical systems, so that the inspection apparatus becomes bulkier and requires a larger electric power consumption.

SUMMARY OF THE INVENTION

An object of the present invention to provide a foreign particle inspection apparatus capable of accurate foreign particle inspection with plural light-receiving optical systems, even when the range of inspection is expanded. Another object of the present invention is to provide a foreign particle inspection apparatus in which the signal processing system is not complicated even in case the number of the light-receiving optical systems is increased, corresponding to the expansion of the range of inspection.

The above-mentioned objects can be attained, according to the present invention, by a foreign particle inspection apparatus comprising:

an illuminating system for irradiating an inspection area on a specimen with an inspecting light;

plural light-receiving optical systems which are adapted to condense the scattered light generated from a foreign particle present in said inspection area upon the irradiation with said inspecting light, and each of which has a light-receiving area, on said specimen, smaller than said inspection area;

a foreign particle detection system for detecting the foreign particle on said inspection area, based on the lights condensed by said plural light-receiving optical system;

wherein said plural light-receiving optical systems are so positioned that the light-receiving area of each light-receiving optical system partially overlaps with at least one other light-receiving area and any point in said inspection area is present in the light-receiving areas of at least two among said plural light-receiving optical systems.

In the above-explained configuration, for receiving the scattered light generated by the foreign particle in the inspection area from the irradiating inspection light, there are provided plural light-receiving optical systems in such a manner that their light-receiving areas mutually overlap partially, so that, even when the inspection area is expanded, accurate foreign particle inspection can be achieved by simply increasing the number of the light-receiving optical systems, without increasing the size of an individual light-receiving optical system. It is also possible to exactly distinguish the foreign particle from the pattern which is not the object of inspection, for example by determining the logic product of the photoelectric signals obtained by the lights condensed by the light-receiving optical system of which light-receiving areas mutually overlap partially.

DESCRIPTION OF THE PREFERRED EMBODIMENTS

Now the foreign particle inspection apparatus of the present invention will be described in detail, with reference to the preferred embodiments thereof shown in the attached drawings.

[1st embodiment]

Figure 1:
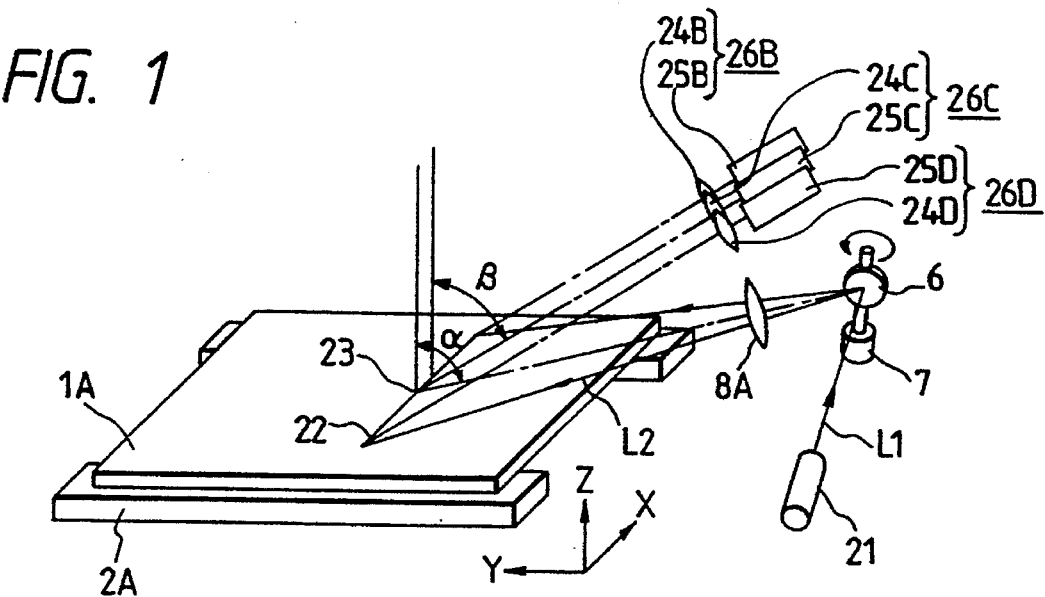
FIG. 1 is a perspective view of principal parts, showing the positional relationship between a light beam scanning system and a light-receiving system, in a first embodiment of the foreign particle inspection apparatus of the present invention.

FIG. 1 shows the principal parts of a foreign particle inspection apparatus constituting a 1st embodiment of the present invention. A light beam L1 emitted from a light source 21 such as a laser light source is deflected for scanning by a galvano scanning mirror 6 toward a scanning lens 8A, and a light beam L2 emerging therefrom scans the surface of a reticle 1A, along a scanning line 22 in the X-direction. Said reticle 1A is placed on a stage 2A, which is moved by an unillustrated drive unit in the Y-direction perpendicular to the X-direction. The entire surface of the reticle 1A is inspected for the foreign particle, by moving the stage 2A in the Y-direction with a certain constant speed, in synchronization with the scanning operation of the light beam L2, by the galvano scanning mirror 6, along the scanning line 22 in the X-direction.

Along the scanning line 22 there are provided light-receiving systems 26B–26D, including imaging lenses 24B–24D and photodetectors 25B–25D such as photomultipliers. In the present embodiment there are in fact provided six light-receiving systems 26A–26F (cf. FIG. 2), of which only three are illustrated in FIG. 1. The scattered light from the reticle 1 is received by the light-receiving systems 26A–26F, and the foreign particle on the scanning line 22 is detected by detection signals from the photodetectors 25A–25F of said light-receiving systems 26A–26F.

Referring to FIG. 1, the light beam L2 from the scanning lens 8A is incidenton the surface of the reticle 1 with an incident angle α, while the scattered light from the foreign particle on the reticle 1 enters the light-receiving systems 26A–26F with light-receiving angles (emerging angles to the normal line to the inspected surface) approximately equal to β. The optical systems are so arranged that the incident angle α becomes larger than the light-receiving angle β (α>β).

Figure 2:
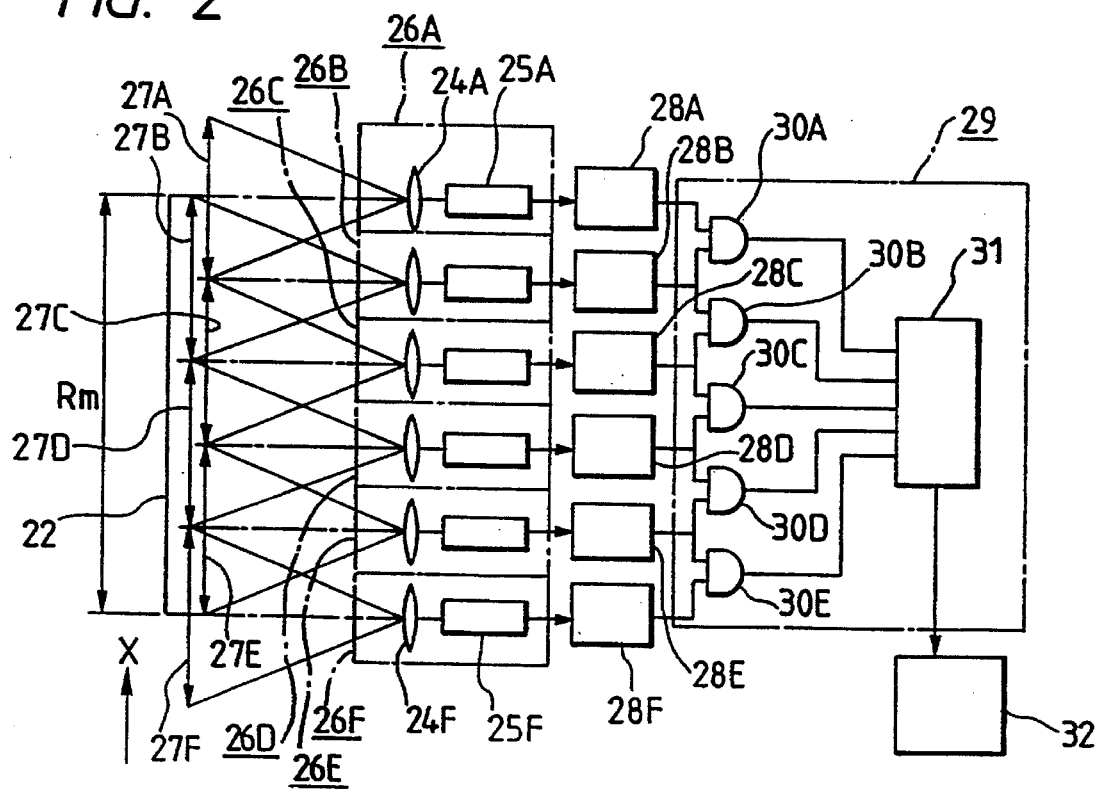
FIG. 2 is a block diagram of light-receiving systems and a signal processing system in the first embodiment.

FIG. 2 shows the detailed configuration of the light-receiving systems and the signal processing system in FIG. 1, wherein the light-receiving systems 26A–26F are composed of imaging lenses 24A–24F and photodetectors 25A–25F positioned therebehind. The areas of generation, along the scanning line 22, of the light to be respectively received by said light-receiving systems 26A–26F, namely the inspection areas 27A–27F, have the same width in the scanning direction (X-direction). Said inspection areas 27A–27F are so designed that, for the mutually neighboring light-receiving systems (for example 26A and 26B), the corresponding inspection areas (for example 27A and 27B) mutually overlap by a predetermined width in the X-direction, but each of the inspection areas 27A–27F corresponding to the light-receiving systems 26A–26F does not overlap with the inspection area of a light-receiving system next to an adjacent one. For example the inspection area 27C of the light-receiving system 26C is so arranged as not to overlap with the inspection areas 27A, 27E of the light-receiving systems 26A, 26E which are next to the inspection areas adjacent to inspection areas 27B, 27D. In the present embodiment, the light-receiving systems 26A–26F are so arranged that each of the inspection areas 27A–27F overlaps with the adjacent one, in the X-direction, by ½ of the width in the X-direction.

Figure 3A:
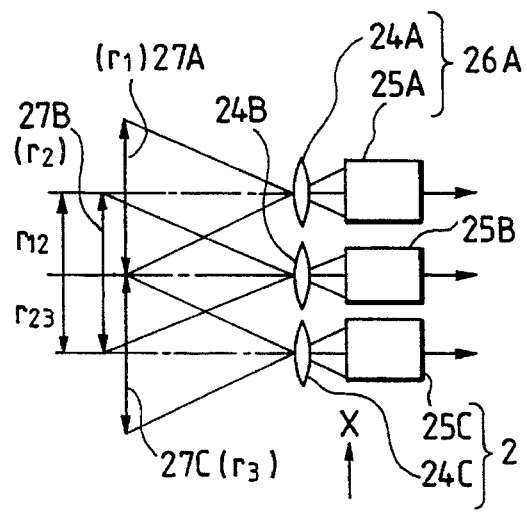
FIG. 3A is a magnified view showing the positional relationship of three light-receiving systems in FIG. 2.

FIG. 3A is a magnified view of the light-receiving systems 26A–26C in FIG. 2. The inspection area 27A of a width $r_1$ in the scanning direction (X-direction) and the inspection area 27B of a width $r_2$ ($=r_1$) overlap to define a partial inspection area having a width $r_{12}$ in the X-direction, and the light from said partial inspection area is received by the light-receiving systems 26A and 26B. Similarly, the light from a partial inspection area of a width $r_{23}$, defined by overlapping of the inspection areas 27B and 27C is received by the light-receiving systems 26B and 26C. Said width $r_{12}$ and $r_{23}$ are equal to $r_1/2$.

Figure 3B:
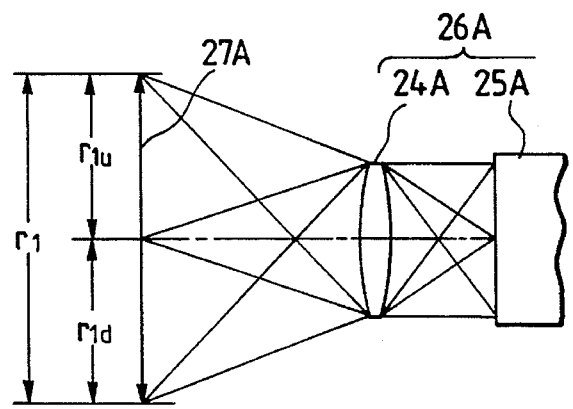
FIG. 3B is a partially cut-off magnified view, showing the mode of light condensation in a light-receiving system shown in FIG. 2.

FIG. 3B shows the relationship between a light-receiving system 26A and an inspection area 27A. As shown in this drawing, the image of the inspection area 27A of a width $r_1$ is focused, by an imaging lens 24A, on the light-receiving face of the photodetector 25A. Therefore, if light is scattered by a foreign particle present in the inspection area 27A, the image (scattered light) of said foreign particle is subjected to photoelectric conversion by the photodetector 25A. In the present embodiment, however, since the position of the foreign particle in the X-direction is detected by the deflection angle of the galvano scanning mirror 6 shown in FIG. 1, the photodetector 25A need not be an image sensor but is only required to effect photoelectric conversion on the entire received light. In the inspection area 27A, the light from the upper half area of a width $r_{1u}$ and that from lower half area of a width $r_{1d}$ are both photoelectrically converted by the photo-detector 25A. Other light-receiving systems 26B–26F are also similarly constructed.

Again referring to FIG. 2, there are thus formed, along the scanning line 22 of a width Rm, five partial inspection areas having a width of $r_1/2$ each and covering the entire scanning line 22 without interruption. Consequently the scanning line 22 of the width Rm represents the effective inspection range on the reticle 1 in the X-direction. Areas on both sides of said scanning line 22, i.e. the upper half area of the inspection area 27A and the lower half area of the inspection area 27F are respectively inspected by only one light-receiving system 26A or 26F, but such areas can be disregarded because they are located outside the effective inspection area.

In the signal processing system shown in FIG. 2, detection signals (photoelectrically converted signals) from the photodetectors 25A–25F of the light-receiving systems 26A–26F are respectively supplied to foreign particle signal process units 28A–28F, each of which compares the corresponding detection signal with a threshold value slightly in excess of the noise level, and outputs a binary signal assuming a value "0" or "1" respectively if said detection signal is lower, or not lower than said threshold value. Thus the foreign particle signal process units 28A–28F effect foreign particle identification on a first level of determining the candidates for the foreign particle, by comparing the detection signal with said threshold level.

The binary signals from said foreign particle signal process units 28A–28F are supplied to a foreign particle identification unit 29, provided with five 2-input 1-output AND gates 30A–30E. The binary signal from the foreign particle signal process unit 28A is supplied to an input port of the AND gate 30A, while the binary signal from the foreign particle signal process unit 28B is supplied to the other input port of said AND gate 30A and also to an input port of the AND gate 30B. Also the binary signal from the foreign particle signal process unit 28C is supplied to the other input port of the AND gate 30B and also to an input port of the AND gate 30C, while the binary signal from the foreign particle signal process unit 28D is supplied to the other input port of the AND gate 30C and also to an input port of the AND gate 30D. The binary signal from the foreign particle signal process unit 28E is supplied to the other input port of the AND gate 30D and to an input port of the AND gate 30E. The binary signal from the foreign particle signal process unit 28F is supplied to the other input port of the AND gate 30E.

Thus, in the present embodiment, the presence of a foreign particle is identified in case the binary signals from the adjacent two foreign particle signal process units (for example 28A and 28B) both assume the high-level state "1". The light (diffracted light) from the circuit pattern formed on the reticle 1A is usually directional, so that the probability of receiving such light from the circuit pattern simultaneously by two adjacent light-receiving systems (for example 26A and 26B) is low. On the other hand, as the light scattered by the foreign particle is substantially isotropic, the probability of simultaneously receiving such scattered light with two adjacent light-receiving systems is high. It is therefore possible to distinguish the foreign particle and the circuit pattern on the reticle and to detect the foreign particle only, by supplying each of the AND gates 30A–30E with binary signals obtained from the detection signals of the two adjacent light-receiving systems.

The output signals of said five AND gates 30A–30E are supplied to a combined discrimination unit 31, which generates, for example by the logic sum of said five output signals, the information on the foreign particles within the entire width of the scanning line 22 in the X-direction. Though not illustrated, the combined discrimination unit also receives the deflection angle signal supplied to the galvano scanning mirror 6 and the measurement signal indicating the X-coordinate of the stage 2A, and determines the coordinates (X, Y) of the foreign particle from said deflection angle signal and said measurement signal when the logic sum of said five output signals assumes the high-level state "1". The information of thus determined coordinates (X, Y) of the foreign particle is stored in a memory 32.

It is also possible to classify the foreign particles in size in the combined discrimination unit 31, utilizing a fact that the duration of the high-level state "1" becomes longer in the output signals of the AND gates 30A–30E for larger foreign particles, and to store the size information of the foreign particles in the memory 32. Based on the information stored in the memory 32, information on the foreign particles present on the reticle 1 can be displayed, on substantially real-time basis, for example on a CRT display (not shown).

In the first embodiment, as explained in the foregoing, the inspection areas 27A–27F of the light-receiving systems 26A–26F, successively overlapping by ½ in the X-direction as described, cover the entire range of the scanning line 22. Consequently, even if the scanning line 22 is long in the X-direction, each of the inspection areas 27A–27F of the light-receiving systems 26A–26F can be made narrow, so that compactness of the light-receiving systems 26A–26F as well as the entire optical system can be achieved. Furthermore, any point in the entire range of the scanning line 22 belongs to an overlapping area of the inspection areas (for example 27A and 27B) of two light-receiving systems (for example 26A and 26B), so that the foreign particle and the circuit pattern can be distinguished in highly accurate manner, by determining the logic product of the binary signals obtained from the detection signals of two adjacent light-receiving systems.

In FIG. 2, there are provided six light-receiving systems 26A–26F along the scanning line 22, but there can be employed two or more light-receiving systems of any arbitrary number. The foreign particle identification unit 29 shown in FIG. 2 obtains the logic product of the binary signals from the adjacent foreign particle signal process units (for example 28A and 28B), but there may be utilized instead the logic sum for example in case the surface of the inspected specimen does not have the circuit pattern or the like. Such logic sum allows to detect, with a high probability, a foreign particle showing certain directionality in the scattered light.

[2nd embodiment]

In the following a 2nd embodiment of the present invention will be explained with reference to FIG. 4. The present embodiment is featured by simplification of the signal processing system, shown in FIG. 2, of the 1st embodiment, and components in FIG. 4 corresponding to those in FIG. 2 are represented by corresponding numbers and will not be explained further.

Figure 4:
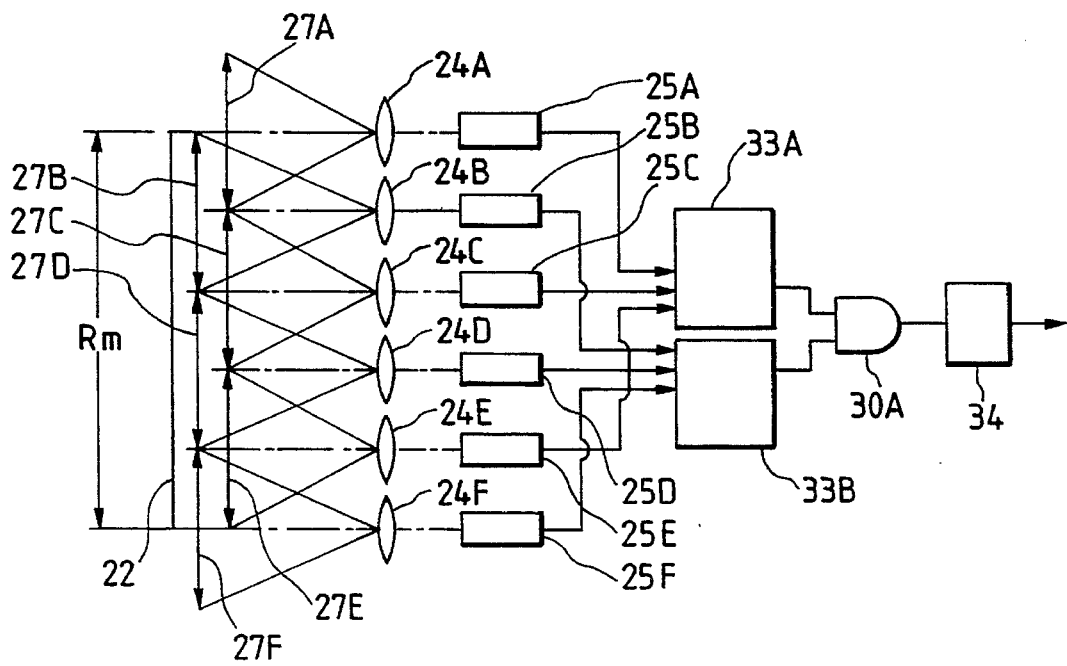
FIG. 4 is a block diagram of light-receiving systems and a signal processing system in a second embodiment of the present invention.

FIG. 4 shows the light-receiving systems and the signal processing system of the 2nd embodiment. Along the scanning line 22, there are arranged six light-receiving systems including respective of imaging lenses 24A–24F and photodetectors 25A–25F, and said scanning line 22 is covered in overlapping manner, as in the 1st embodiment, by the inspection areas 27A–27F of said light-receiving systems.

In the present embodiment, the detection signals of three alternate photodetectors 25A, 25C and 25E are supplied to a first foreign particle signal process unit 33A, while those of the remaining three photodetectors 25B, 25D and 25F are supplied to a second foreign particle signal process unit 33B. Each of the foreign particle signal process units 33A, 33B is provided with an addition circuit for three detection signals, and a comparator for comparing the output signal of said addition circuit with a threshold value exceeding the noise level, and is adapted to output a binary signal "1" or "0" respectively when the sum of the three detection signals exceeds or does not exceed said threshold level. The binary signals from the two foreign particle signal process units 33A, 33B are supplied to two input ports of an AND gate 30A, of which output signal is supplied to a foreign particle identification unit 34. Said foreign particle identification unit 34 detects the foreign particle, based on the output signal of the AND gate 30A, in the same manner as in the combined discrimination unit 31 in FIG. 2.

In the present embodiment, when the laser beam scans, for example, the overlapping area of the inspection areas 27A and 27B on the scanning line 22, the scattered light from a foreign particle in said overlapping area can only be received by the photodetectors 25A and 25B. Consequently, if a foreign particle is present in said overlapping area, the detection signal of the photodetector 25A supplied to the foreign particle signal process unit 33A and that of the photodetector 25B supplied to the process unit 33B alone assume a level indicating such foreign particle, while the detection signals from other photodetectors 25C–25F become lower than a predetermined level.

Also in case a foreign particle is present in the overlapping area of the inspection areas 27B and 27C, the detection signal of the photodetector 25C supplied to the foreign particle signal process unit 33A and that of the photodetector 25B supplied to the process unit 33B alone assume a level indicating such foreign particle. Thus, generally, in case a foreign particle is present at any point on the scanning line 22, the level indicating such foreign particle is assumed by only one among the respective three detection signals supplied to each of the foreign particle signal process units 33A and 33B.

Consequently the foreign particle signal process unit 33A outputs a binary signal corresponding to the sum signal of the binary signals from the foreign particle signal process units 28A, 28C, 28E in FIG. 2, and the foreign particle signal process unit 33B outputs a binary signal corresponding to the sum signal of the binary signals from the process units 28B, 28D, 28F shown in FIG. 2. The AND gate 30A outputs a signal assuming a level "1" only when the binary signals from the foreign particle signal process units 33A, 33B are both at the high-level state "1", namely only when adjacent light-receiving systems (for example those containing the imaging lenses 24A and 24B) simultaneously receive the scattered light from the foreign particle. In this manner the AND gate 30A can distinguish the foreign particle from the circuit pattern.

The present embodiment can simplify the signal processing system, as the number of the foreign particle signal process units 33A, 33B is reduced to ⅓ in comparison with the configuration shown in FIG. 2, and the number of AND gates is reduced to ⅕ in comparison with the configuration in FIG. 2. Also the addition circuits in the foreign particle signal process units 33A, 33B can be made smaller than the summing circuit in the combined discrimination unit 31 in FIG. 2. Also in the present embodiment, there may be employed more than six light-receiving systems.

[3rd embodiment]

In the following there will be explained a 3rd embodiment of the present invention, with reference to FIG. 5. The present embodiment is to simplify the light-receiving systems and the signal processing system of the 1st embodiment, and, in FIG. 5, components corresponding to those in FIGS. 2 and 4 are represented by corresponding numbers and will not be explained further.

Figure 5:
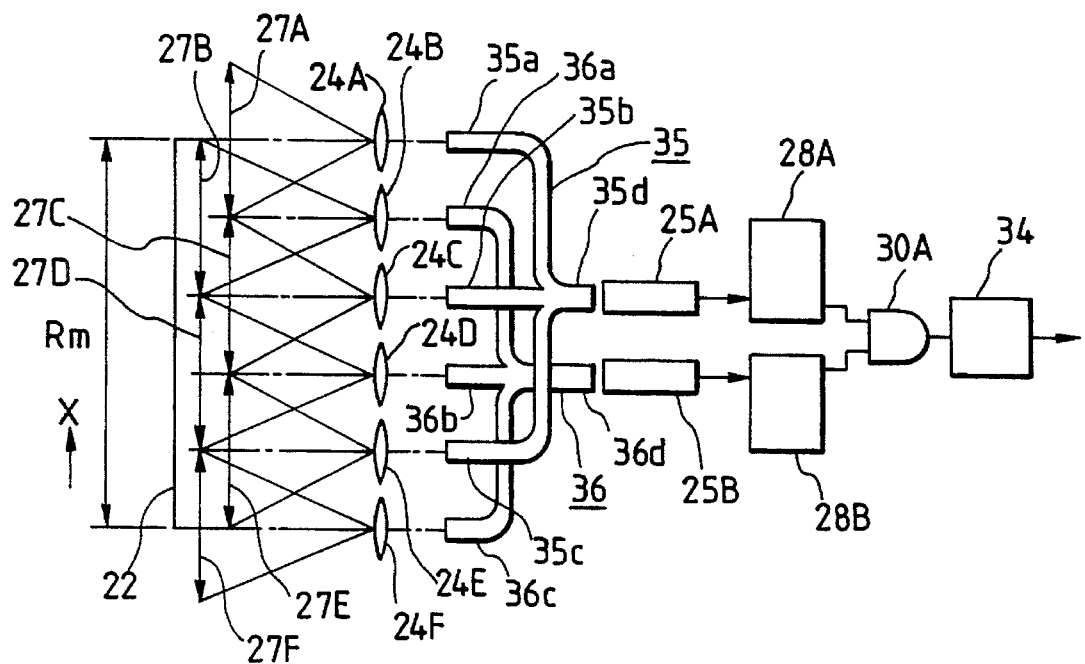
FIG. 5 is a block diagram of light-receiving systems and a signal processing system in a third embodiment of the present invention.

FIG. 5 shows the light-receiving systems and the signal processing system of the 3rd embodiment. Along the scanning line 22, there are provided six imaging lenses 24A–24F, and the scanning line is covered in overlapping manner, as in the 1st embodiment, by the inspection areas 27A–27F corresponding to these imaging lenses.

The present embodiment employs optical fiber bundles 35, 36 each having three entrance ends and an exit end. The entrance ends 35a, 35b, 35c of the first optical fiber bundle 35 are respectively placed at the focal planes of alternate imaging lenses 24A, 24C, 24E, and the exit end 35d of said optical fiber bundle 35 is placed immediately in front of the light-receiving face of the photodetector 25A. Similarly the entrance ends 36a, 36b, 36c of the second optical fiber bundle 36 are respectively placed at the focal planes of alternate imaging lenses 24B, 24D, 24F, and the exit end 36d of said optical fiber bundle 36 is placed immediately in front of the light-receiving face of the photodetector 25B.

Thus the lights condensed by the imaging lenses 24A, 24C, 24E are guided by the optical fiber bundle 35 to the photodetector 25A, while those condensed by the lenses 24B, 24D, 24F are guided by the optical fiber bundle 36 to the photodetector 25B. The detection signals of the photodetectors 25A, 25B are respectively supplied to the foreign particle signal process units 28A, 28B, which in turn supply binary signals to the AND gate 30A, of which output signal is supplied to the foreign particle discrimination unit 34.

In the present embodiment, among the imaging lenses 24A–24F, the scattered light from the foreign particle at an arbitrary position on the scanning line 22 can be guided, to the entrance ends of the optical fiber bundles 35, 36, only by two adjacent lenses (for example 24A and 24B). Consequently, among three entrance ends 35a–35c or 36a–36c of the optical fiber bundle 35 or 36, only one or less receives light indicating the presence of foreign particle, and each of the optical fiber bundles 35, 36 can effect addition without intermixing of the scattered light from the scanning line 22.

The detection signals output from the photodetectors 25A, 25B when a foreign particle is present correspond to the lights condensed by two adjacent imaging lenses among the lenses 24A–24F, and the signal from the AND gate 30A is equal to the logic sum of the signals output from the five AND gates 30A–30E shown in FIG. 2. It is therefore possible to distinguish the circuit pattern from the foreign particle and to accurately detect only the foreign particle on the scanning line 22.

In comparison with the 1st embodiment shown in FIG. 2, the present embodiment reduces the number of photodetectors to $\frac{1}{3}$, that of foreign particle signal process units to $\frac{1}{3}$, and that of AND gates to $\frac{1}{5}$, thereby achieving significant simplification of the signal processing system. Also the use of the optical fiber bundles simplifies and reduces the size of the light-receiving systems. Also, if the scanning line 22 is expanded in the X-direction, there can be added lenses which are the same as lenses 24A–24F in similarly displaced positions, and there can be employed optical fiber bundles with a larger number of entrance ends, instead of the bundles 35, 36. The signal processing systems need not be expanded and can therefore be compact.

[4th embodiment]

In the following a 4th embodiment of the present invention will be explained with reference to FIG. 6. In contrast to the 1st embodiment in which the inspection areas 27A–27F are arranged with an interval of ½ of the width of said areas, along the scanning line 22, the present embodiment employs inspection areas 38A–38F arranged, along the scanning line 22, with an interval of ⅓ of the respective width of said areas. Components in FIG. 6, corresponding to those in FIGS. 2 and 4, are represented by corresponding numbers and will not be explained further.

Figure 6:
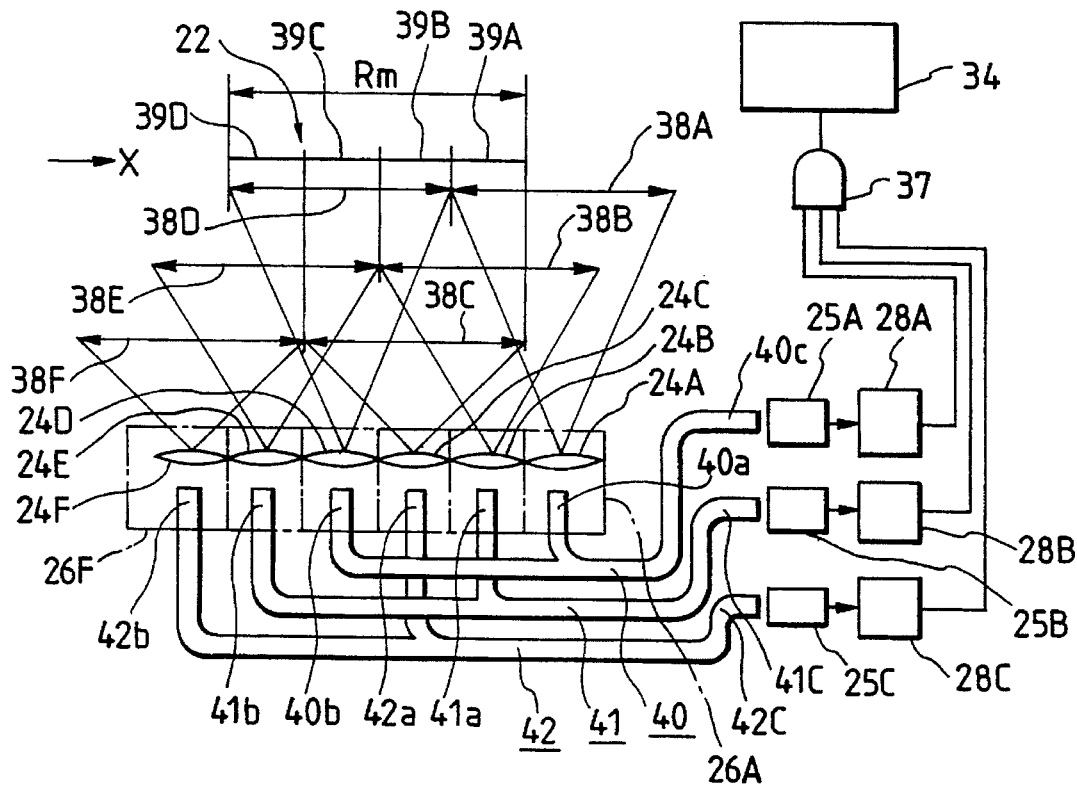
FIG. 6 is a block diagram of light-receiving systems and a signal processing system in a fourth embodiment of the present invention.

FIG. 6 shows the light-receiving system and the signal processing systems of the 4th embodiment. Along the scanning line of a width Rm, there are arranged six imaging lenses 24A–24F, defining the inspection areas 38A–38F of a same width in the X-direction. The inspection areas 38B–38F are formed by displacing the areas 38A–38E by ⅓ of the width in the X-direction. The 1st inspection area 38A is so positioned that ⅓ of the width thereof is on the scanning line 22, and the 6th inspection area 38F is likewise positioned. The overlapping area of the first three inspection areas 38A–38C defines a first partial inspection area 39A. Similarly the overlapping areas of the three inspection areas 38B–38D, 38C–38E and 38D–38F respectively define partial inspection areas 39B, 39C and 39D. The scanning line 22 is covered, without interruption, by the four partial inspection areas 39A–39D, and corresponds to the effective inspection range.

The present embodiment employs optical fiber bundles each having two entrance ends and an exit end. Entrance ends 40a, 40b of a first optical fiber bundle 40 are respectively placed at the focal planes of the imaging lenses 24A, 24D, and an exit end 40c of said bundle 40 is placed immediately in front of the light-receiving face of the photodetector 25A. Thus the lights condensed by said lenses 24A, 24D are guided by the optical fiber bundle 40 to the photodetector 25A. Similarly the entrance ends 41a, 41b of a second optical fiber bundle 41 are placed respectively at the focal planes of the imaging lenses 24B, 24E, and the exit end 41c is placed immediately in front of the light-receiving face of the photodetector 25B. Also the entrance ends 42a, 42b of a third optical fiber bundle are respectively placed at the focal planes of the imaging lenses 24C, 24F, and the exit end 42c is placed immediately in front of the light-receiving face of the photodetector 25C. The light-receiving systems 26A–26F are composed of the imaging lenses 24A–24F and the entrance ends of the optical fiber bundles positioned at the image planes of said lenses.

The detection signals of the photodetectors 25A–25C are respectively supplied to the foreign particle signal process units 28A–28C, which in turn supply binary signals to input ports of a 3-input AND gate 37, supplying the output signal to the foreign particle discrimination unit 34. The foreign particle signal process units 28A–28C effect preliminary detection of the foreign particle according to whether the detection signal is higher than a predetermined threshold level.

In the present embodiment, among the imaging lenses 24A–24F, the scattered light from a foreign particle present in a partial inspection area 39A on the scanning line 22 is guided to the entrance ends of the optical fiber bundles 40–42, only by three adjacent lenses 24A–24C. The lights condensed by said three lenses 24A–24C are subjected, without intermixing, to photoelectric conversion by the photodetectors 25A–25C, and the AND gate 37 determines the logic product of the binary signals obtained by the foreign particle signal process units 28A–28C, corresponding to said photoelectrically converted signals. Similarly the scattered light from the foreign particle at an arbitrary point on the scanning line 22 is subjected to photoelectric conversion by the corresponding three imaging lenses, and the corresponding binary signals are used for obtaining the logic product.

Consequently, in the present embodiment, the presence of a foreign particle is identified only when the scattered light from the foreign particle is received by three adjacent lenses (for example 24A–24C). If a circuit pattern is present on the scanning line 22 and the diffracted light from said circuit pattern is received by two adjacent imaging lenses, for example, the detection of the foreign particle will not take place by the calculation of the logic product. Consequently there is attained an improved accuracy of distinguishing between the foreign particle and the proper circuit pattern present on the reticle.

In case the scanning line 22 becomes wider in the configuration shown in FIG. 6, there can be added imaging lens or lenses the same as lenses 24A–24F, at the same interval, and there can be employed optical fiber bundles with a larger number of entrance ends, instead of the bundles 40–42. Consequently the signal processing systems need not be expanded and can be compact.

If the inspected specimen does not bear the circuit pattern or the like, it is also possible, as in the first embodiment, to employ an OR gate instead of the AND gate 37A shown in FIG. 6, thereby obtaining the logic sum of the binary signals from the three foreign particle signal process units 28A–28C. Such configuration improves the sensitivity of detection for the foreign particle present on the scanning line 22.

In the foregoing embodiments, the neighboring inspection areas overlap by ½ or ⅓ of the width of said inspection areas. Such arrangement can be defined in more general terms in the following manner. In a series of inspection areas, corresponding to the light-receiving systems and having a same width x in the scanning direction, with respect to the inspection area of a 1st light-receiving system, the inspection area of a 2nd light-receiving system, adjacent to said 1st system, is so positioned as to obtain an overlapping by $((n-1)/n)x$, wherein n is an integer at least equal to 2. Also the inspection area of a 3rd light-receiving system, positioned adjacent to the 2nd system, is so positioned as to obtain an overlapping by $((n-2)/n)x$ with the inspection area of the 1st light-receiving system and an overlapping by $((n-1)/n)x$ with the inspection area of the 2nd light-receiving system. Similarly, the inspection area of an $n_i$-th light-receiving system ($n_i$ being an integer at least equal to 4) is so positioned as to obtain an overlapping by $((n-n_i)/n)x$ with the inspection area of the 1st light-receiving system.

In such configuration, each point on the scanning line belongs to the overlapping area of the inspection areas of n adjacent light-receiving systems. It is therefore possible to distinguish the foreign particle to be inspected and the circuit pattern which is not to be detected, in highly accurate manner, by calculating the logic product of the binary signals obtained from the photoelectric signals of the n adjacent light-receiving systems. However, if such circuit pattern is not a problem, there may also be calculated the logic sum of the n binary signals. Also the lights condensed by the light-receiving systems mutually separated by n can be collectively subjected to photoelectric conversion by means of a light guide and a photodetector as shown in FIG. 6 (showing a case of n=3), so that the entire signal processing system can be composed of n photodetectors, n foreign particle signal process units, an n-input AND (or OR) gate and a foreign particle discrimination unit.

Consequently, the size of the circuitry of the signal processing system can be significantly reduced in comparison with the case in which the photodetectors are provided respectively for all the light-receiving systems. Also, according to the present embodiment, the size of the signal processing system can remain same, even in case the number of the light-receiving systems increases, by merely increasing the number of the entrance ends of the light guide, so that the same signal processing system can be used even for a wider inspection range for the foreign particle.

[5th embodiment]

In the following there will be explained a 5th embodiment of the present invention, with reference to FIG. 7, in which components corresponding to those in FIG. 2 are represented by corresponding numbers and will not be explained further.

Figure 7:
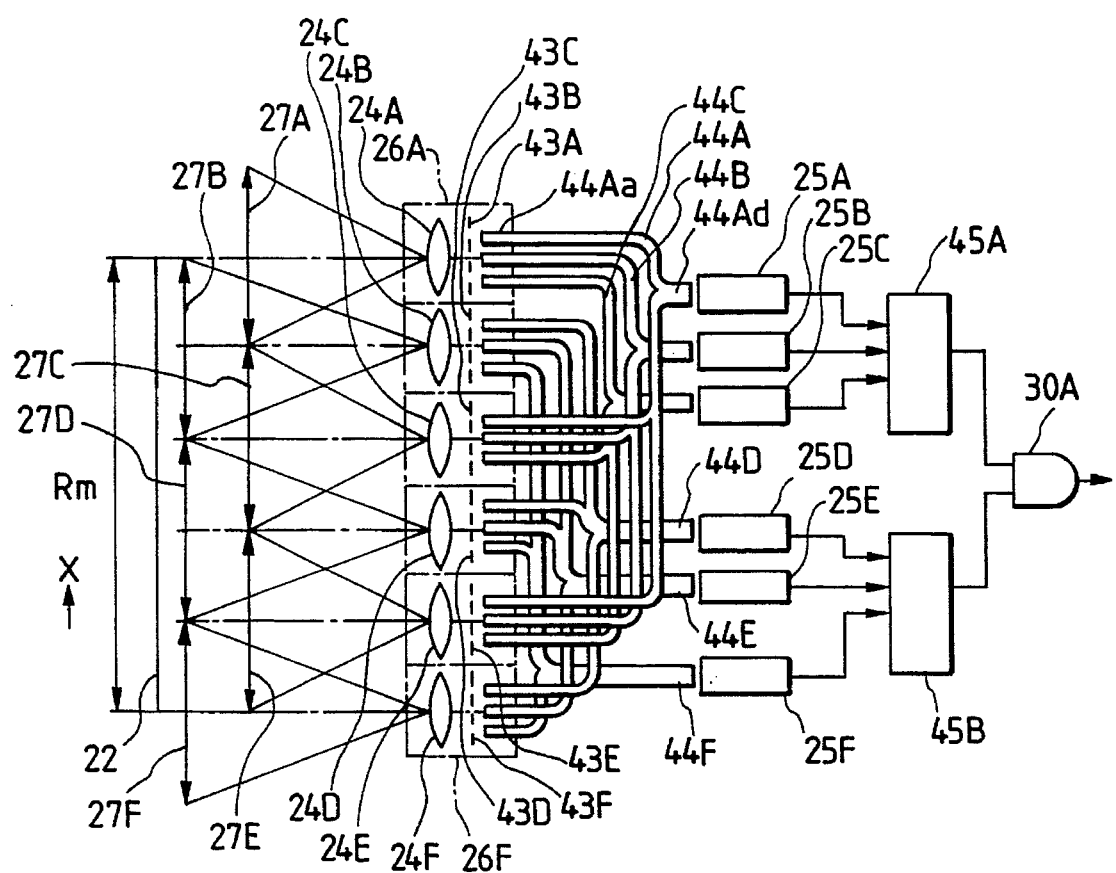
FIG. 7 is a block diagram of light-receiving systems and a signal processing system in a fifth embodiment of the present invention.

FIG. 7 shows the light-receiving systems and the signal processing system of the 7th embodiment, in which, along the scanning line 22 of a width Rm, there are provided six imaging lenses 24A–24F whereby the scanning line 22 is covered, in overlapping manner, by the inspection areas 28A–28F corresponding to said imaging lenses. Also at the pupil planes (Fourier transformation planes) of said imaging lenses 24A–24F, there are respectively provided slit plates 43A–43F, each having plural slits (three slits in case of FIG. 7). The present embodiment employs six optical fiber bundles 44A–44F, each having three entrance ends and an exit end, for individually receiving the lights transmitted by the slits of said slit plates 43A–43F.

More specifically, the lights transmitted by the 1st slits of the slit plates 43A, 43C, 43E at the pupil planes of the imaging lenses 24A, 24C, 24E are guided by an optical fiber bundle 44A to the photodetector 25A. Also the lights transmitted by the 2nd slits are guided by an optical fiber bundle 44B to the photodetector 25B, and the lights transmitted by the 3rd slits are guided by an optical fiber bundle 44C to the photodetector 25C. For example the 1st entrance end 44Aa of the optical fiber bundle 44A is positioned immediately behind the 1st slit of the pupil-dividing slit plate 43A, and the exit end 44Ad of said optical fiber bundle is positioned opposite to the light-receiving face of the photodetector 25A.

Also the lights transmitted by the 1st slits of the pupil-dividing slit plates 43B, 43D, 43F at the pupil planes of the imaging lenses 24B, 24D, 24F are guided by an optical fiber bundle 44D to the photodetector 25D, while the lights transmitted by the 2nd slits are guided by an optical fiber bundle 44E to the photodetector 25E, and the lights transmitted by the 3rd slits are guided by an optical fiber bundle 44F to the photodetector 25F. In the present embodiment, the light-receiving systems 26A–26F are composed of the imaging lenses 24A–24F, slit plates 43A–43F and corresponding entrance ends of the optical fiber bundles.

The detection signals of the photodetectors 25A–25C are supplied to three input ports of a foreign particle signal process unit 45A, while those of the photodetectors 25D–25F are supplied to three input ports of a foreign particle signal process unit 45B. Each of said units 45A, 45B effects preliminary foreign particle detection according to whether a pre-designated one of the supplied three detection signals is higher than a predetermined threshold level. More specifically, in each of said units 45A, 45B, there is generated a binary signal assuming a value "1" or "0" respectively if the pre-designated detection signal is larger than the threshold level or not, and each of said units 45A, 45B generates, for supply to the AND gate 30A, a foreign particle detection signal assuming a high-level state "1" if all the binary signals corresponding to the designated detection signals are at the high-level state "1", or a low-level state "0" if otherwise. For example, if three detection signals are designated, each of the foreign particle signal process units 45A, 45B provides the AND gate 30A with a foreign particle detection signal assuming a high-level state "1" when all the binary signals corresponding to the three input detection signals are in the high-level state "1".

Also in the present embodiment, the scattered light from each point on the scanning line 22 is received by two adjacent light-receiving systems (for example 26A and 26B). However, this does not cause confusion because each of the optical fiber bundles is arranged to perform physical addition of the lights condensed by alternate light-receiving systems. Also the determination of the logic product, by the AND gate 30A, of the binary signals from the foreign particle signal process units 45A and 45B corresponds to the determination of the logic product of the binary signals, corresponding to the lights condensed by the two adjacent light-receiving systems, and the distinguishing between the light from circuit pattern and the light from the foreign particle is achieved by this logic product formation.

In the following there will be explained the functions of the slit plates 43A–43F. Said slit plates function, for example, for distinguishing between the light coming from the circuit pattern and the light from the foreign particle. If the reticle 1 bears a periodical circuit pattern thereon, diffracted light is emitted in a certain direction from such circuit pattern by the scanning with the laser beam. If such diffracted light is transmitted, for example, by the 1st slits of the slit plates 43A–43F, it can be simultaneously detected by the adjacent light-receiving systems (for example 26A and 26B), so that such circuit pattern may be detected as a foreign particle.

In the present embodiment, in such case, the foreign particle signal process units 45A, 45B effect foreign particle detection by the detection signals from the photodetectors 25B, 25C, 25E and 25F, excluding those from the photodetectors 25A and 25D. Such method allows to avoid erroneous detection of the periodical circuit pattern as the foreign particle.

Also as will be apparent from the comparison of FIGS. 7 and 5, in case the inspection areas of the adjacent light-receiving systems (for example 26A and 26B) are arranged with an overlapping of (n−1)/n of the width of each inspection area and m slits are provided in each of the slit plates 43A–43F (m being an integer at least equal to 2) arranged at the pupil planes of the light-receiving systems 26A–26F, the entire signal processing system can be composed of n×m photodetectors, n foreign particle signal process units and an AND gate. Also in case the number of the light-receiving systems 26A–26F is increased for a wider scanning line 22, the signal processing system need not be expanded and there will be no loss in the ability for foreign particle detection.

[6th embodiment]

Figure 8A:
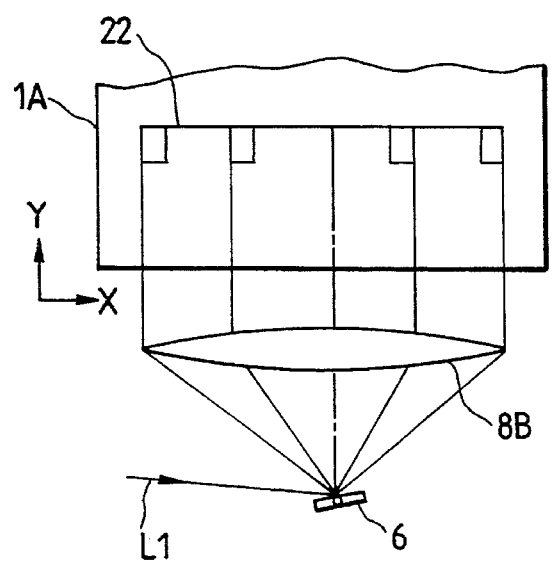
FIG. 8A is a view showing the mode of irradiation with a telecentric scanning optical system.
Figure 8B:
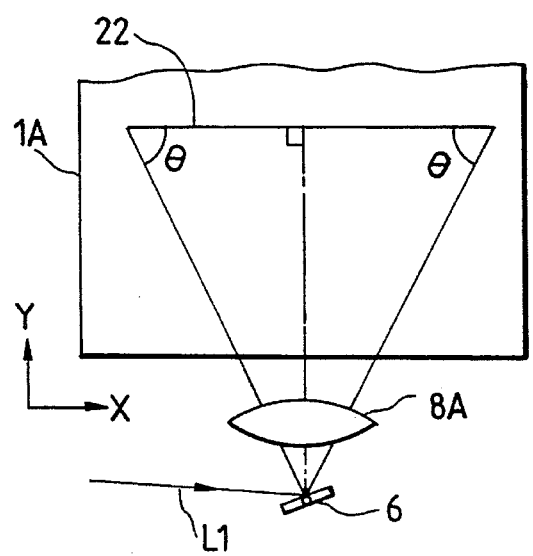
FIG. 8B is a view showing the mode of irradiation with a non-telecentric scanning optical system.

The 6th embodiment employs a telecentric irradiating system for irradiating the scanning line 22 on the reticle 1 with the laser beam. The irradiating system can be classified into a telecentric scanning optical system as shown in FIG. 8A, and a non-telecentric scanning optical system as shown in FIG. 8B. In the telecentric scanning optical system employed in this embodiment, the laser beam L1 is deflected by the galvano scanning mirror 6, then transmitted by a scanning lens 8A and reaches the scanning line 22 on the reticle 1A, parallel to the optical axis of said scanning lens 8A. Consequently the irradiating condition of the laser beam remains constant over the entire scanning line 22.

Figure 9:
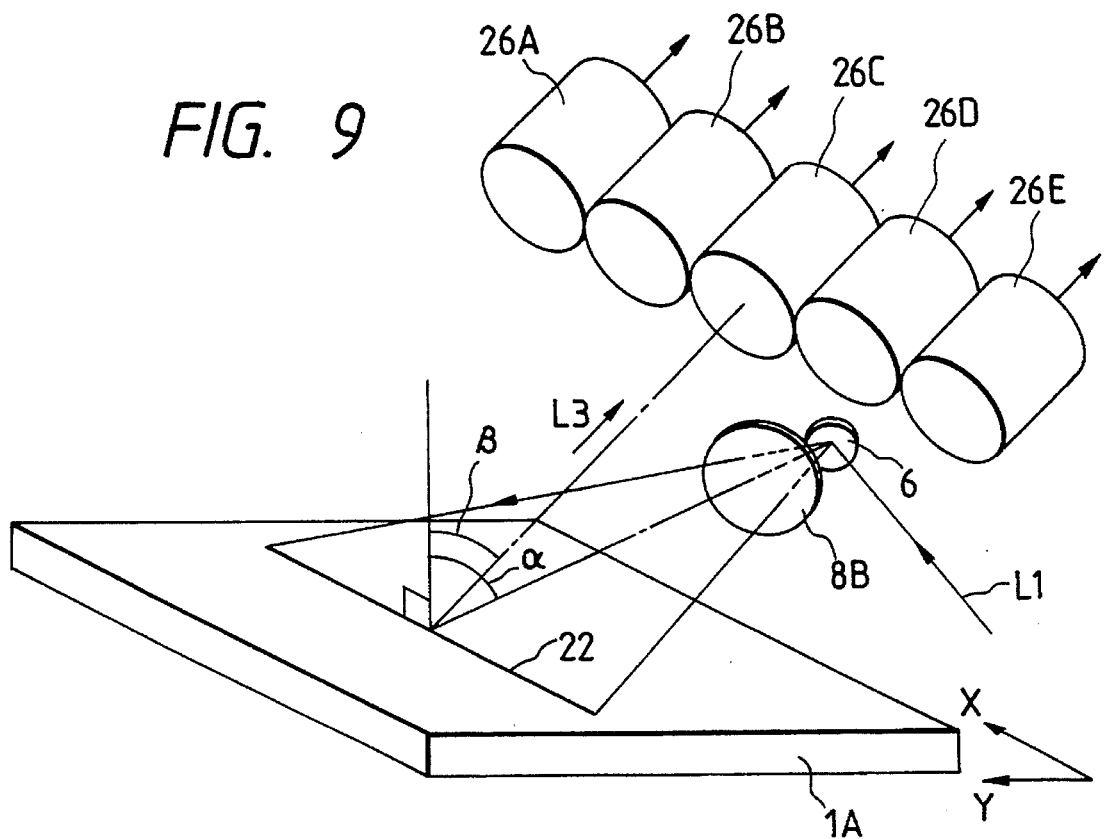
FIG. 9 is a perspective view showing the positional relationship of a light beam scanning optical system and plural light-receiving systems in a sixth embodiment of the present invention.
Figure 10:
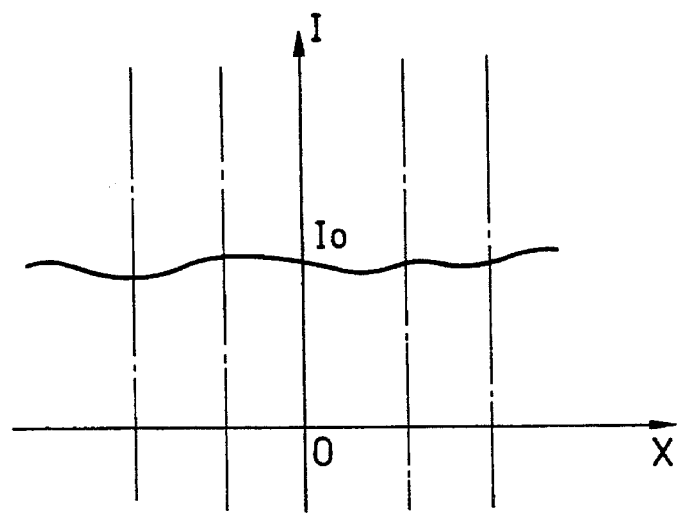
FIG. 10 is a chart showing a sensitivity curve of the light-receiving system in the sixth embodiment.

FIG. 9 shows the arrangement of the light-receiving systems in this embodiment. Five light-receiving systems 26A–26E are so positioned as to oppose to the scanning line 22, with their optical axes in mutually parallel relationship. The laser beam emerging from the scanning lens 8B reaches the scanning line with an incident angle $\alpha$, while the scattered light from the scanning line 22 enters the light-receiving systems 26A–26E with a substantially constant light-receiving angle $\beta$ ($<\alpha$). In such telecentric scanning, the irradiating condition of the laser beam and the light-receiving condition remain same for the light-receiving systems 26A–26E, so that the sensitivity curve (distribution of intensity of detection signal) in the X-direction, or the scanning direction of the light-receiving systems 26A–26E, becomes substantially constant, close to the value $I_0$ at the center, as shown in FIG. 10. Consequently the sensitivity correcting curve in the X-direction becomes a constant straight line for each of the light-receiving systems 26A–26E. As the reticle 1A is moved with a constant speed in the Y-direction, the sensitivity scarcely varies in the Y-direction so that the sensitivity correction is not required in the Y-direction.

The sensitivity distribution in the X-direction can be measured, for example, by substantially uniformly depositing samples of small foreign particles, such as polystyrene spherical beads, on the inspected surface of the reticle 1A in the configuration shown in FIG. 8A and plotting the intensity of the detection signals from the light-receiving systems by the foreign particle inspection on such samples. A sensitivity curve as shown in FIG. 10 can be obtained by plotting the signal intensity I from the light-receiving systems as a function of the X-coordinate determined from the deflection angle signal of the galvano scanning mirror 6 (original point of the X-coordinate being taken on the central line of the reticle 1A). In the configuration shown in FIG. 9, the incident angle $\alpha$ of the laser beam and the light-receiving angle $\beta$ is selected as $\alpha>\beta$, but there may also be adopted a relation $\alpha\leq\beta$.

[7th embodiment]

The 7th embodiment employs a non-telecentric irradiating system for irradiating the scanning line 22 on the reticle 1A with the laser beam.

FIG. 8B illustrates the irradiating system of the present embodiment, in which the entering laser beam L1 enters, through the galvano scanning mirror 6 and the scanning lens 8A, the reticle 1A parallel to the optical axis of the scanning lens 8A at the center of the scanning line 22, but with a certain angle $\Theta$ on both ends of the scanning line 22. Consequently the irradiating condition of the laser beam varies according to the position in the X-direction on the scanning line 22. Also from the side of the light-receiving systems, the one at the center of the scanning line 22 detects the rear scattered light, while those on both ends detect the lights scattered with a certain angle. Thus the light-receiving condition varies depending on the position in the X-direction.

Figure 11:
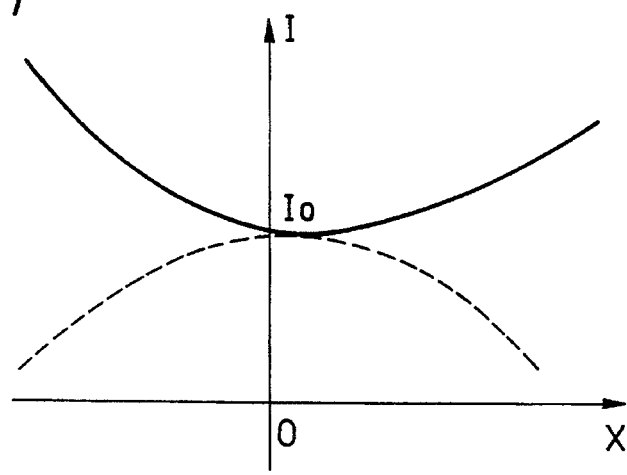
FIG. 11 is a chart showing a sensitivity correcting curve in a first sensitivity correcting method in a seventh embodiment of the present invention.

Also the diameter of the laser beam spot on the reticle 1A varies depending on the position on the scanning line 22 in the X-direction, as the incident angle of the laser beam to the reticle 1A varies. For these reasons, the sensitivity curve in the irradiation with the non-telecentric scanning method shows a significant difference in the sensitivity between the central part and the end parts of the scanning line 22. It is therefore necessary to average the sensitivities of the light-receiving systems, utilizing a sensitivity correction curve obtained from such sensitivity curve. A first sensitivity averaging method utilizing such sensitivity correction curve consists of preparing, as shown in FIG. 11, an entire sensitivity correction curve in the X-direction (solid or broken curve) by continuously connecting the sensitivity correction curves of the light-receiving systems, and collectively correcting the detection signals from the light-receiving systems by such entire sensitivity correction curve. A second method consists of forming, as shown in FIG. 13, individual sensitivity correction curves (broken lines) for respective light-receiving systems and individually correcting the detection signals of the light-receiving systems with such individual sensitivity correction curves.

The first method shown in FIG. 11 is advantageous in that a collective correction is possible, but is incapable of suppressing the sensitivity fluctuations of the respective light-receiving systems, with reference to the reference sensitivity (for example the signal intensity at X=0), so that it is not very useful for fine adjustment. Also as an aberration occurs in the sensitivity at the connecting portion of the light-receiving systems, the correction values for the adjacent light-receiving systems may differ at the boundary therebetween or the aberration in the correction values at such boundary may become significant. Exact correction of sensitivity may become impossible if the sensitivity correction curve becomes discontinuous at the boundary of the neighboring light-receiving systems.

Figure 12:
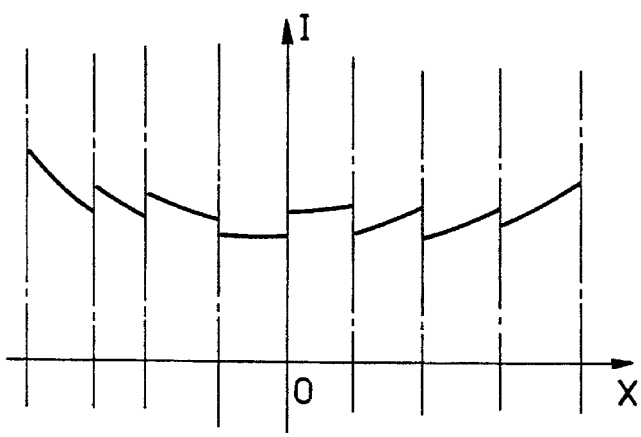
FIG. 12 is a chart showing sensitivity correcting curves for respective light-receiving systems, in a second sensitivity correcting method in a seventh embodiment.
Figure 13:
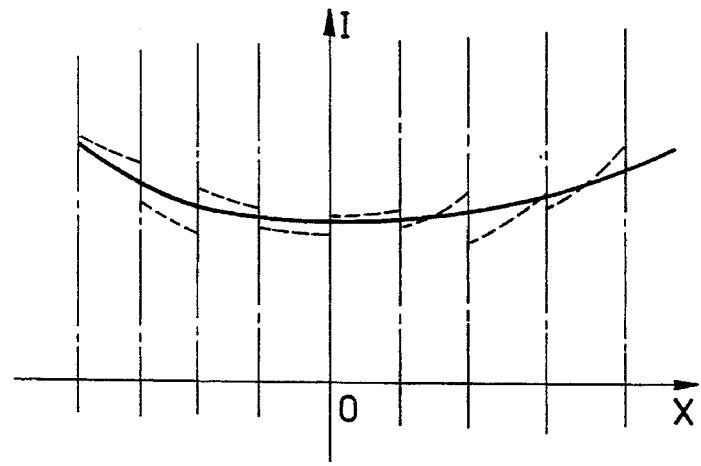
FIG. 13 is a chart showing an entire sensitivity correcting curve for light-receiving systems, in the second sensitivity correcting method in the seventh embodiment.

In contrast, in the second method shown in FIG. 13, the sensitivity is adjusted in the individual light-receiving systems, as indicated by the stepwise varying curve shown in FIG. 12. Consequently, correction beyond the boundary of the adjacent light-receiving system is no longer necessary, and exact correction is possible even if the correction curve is discontinuous at the boundary. Also, even if the sensitivity correction curve is discontinuous at the boundary of the light-receiving systems, the sensitivity distribution after correction becomes substantially uniform without discontinuity.

[8th embodiment]

In the following there will be explained an 8th embodiment of the present invention, with reference to FIG. 14, which shows the arrangement of the light-receiving systems in said 8th embodiment. Laser beam scanning in the telecentric method is conducted along the scanning line 22, along which there are arranged six imaging lenses 24A–24F, with photodetectors 25A–25F respectively therebehind. The scanning line 22 is covered, in overlapping manner, by the inspection areas 27A–27F of said imaging lenses 24A–24F.

In the present embodiment, the optical axes of all the light-receiving systems are not parallel. More specifically, the two light-receiving systems at the center, consisting of the imaging lenses 24C, 24D and the photodetectors 25C, 25D, have optical axes which are mutually parallel and substantially perpendicular to the scanning line 22. However, the first two light-receiving systems positioned outside and consisting of the imaging lenses 24B, 24E and the photodetectors 25B, 25E have optical axes inclined, by an angle $\Theta_2$ to a line perpendicular to the scanning line 22, and the two light-receiving systems positioned further outside and consisting of the imaging lenses 24A, 24F and the photodetectors 25A, 25F have optical axes inclined by an angle $\Theta_1$ ($>\Theta_2$) to the line perpendicular to the scanning line 22. Stated differently, the angle between the optical axis of each light-receiving system and the line perpendicular to the scanning line 22 varies gradually as the distance increases from the center of the scanning line 22. Such inclined optical axes of the light-receiving systems allow to correct the detection sensitivity, thereby alleviating the burden of the signal processing system in the sensitivity correction.

Figure 14:
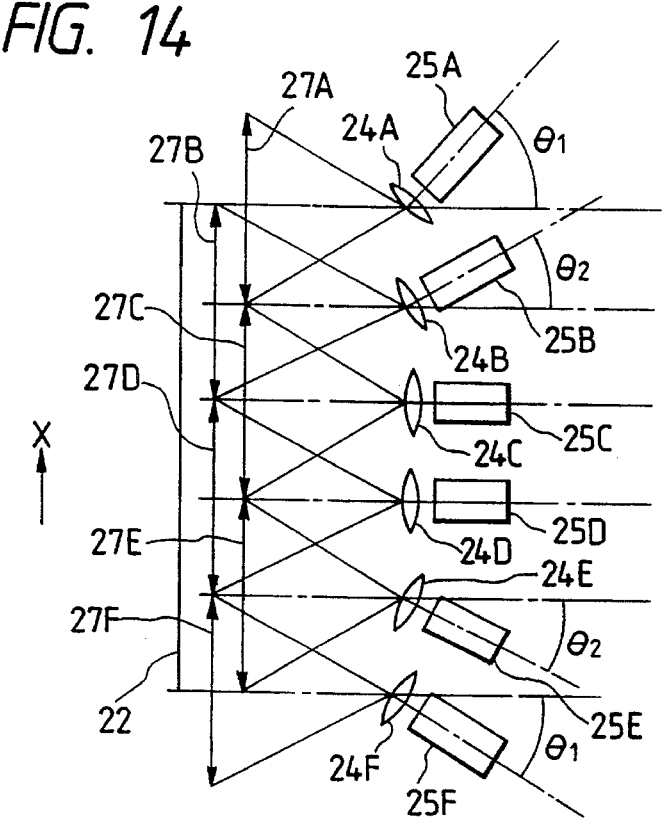
FIG. 14 is a view showing the arrangements of light-receiving systems in an eighth embodiment of the present invention.
Figure 15:
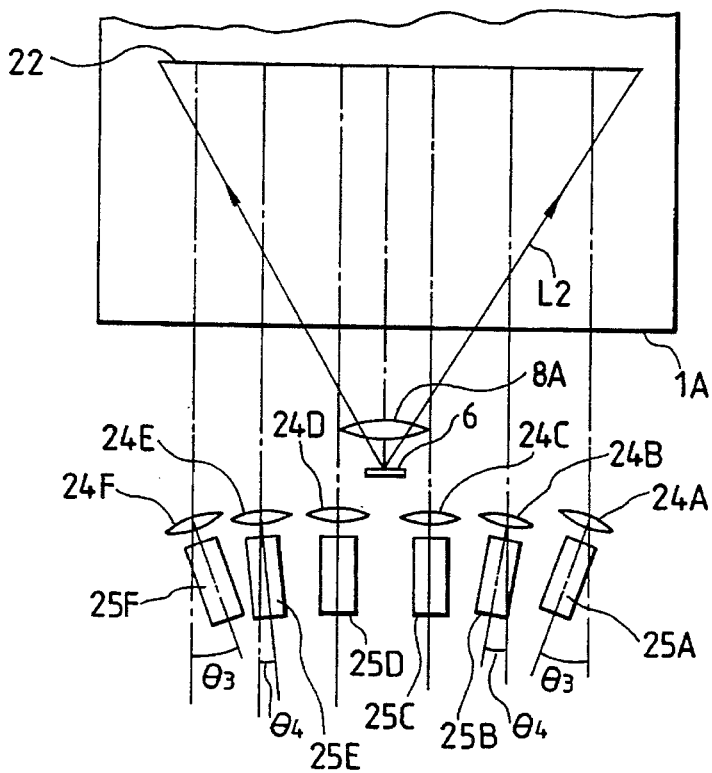
FIG. 15 is a view showing the arrangement of light-receiving systems in an application of the eighth embodiment to a non-telecentric light beam scanning system.
Figure 16:
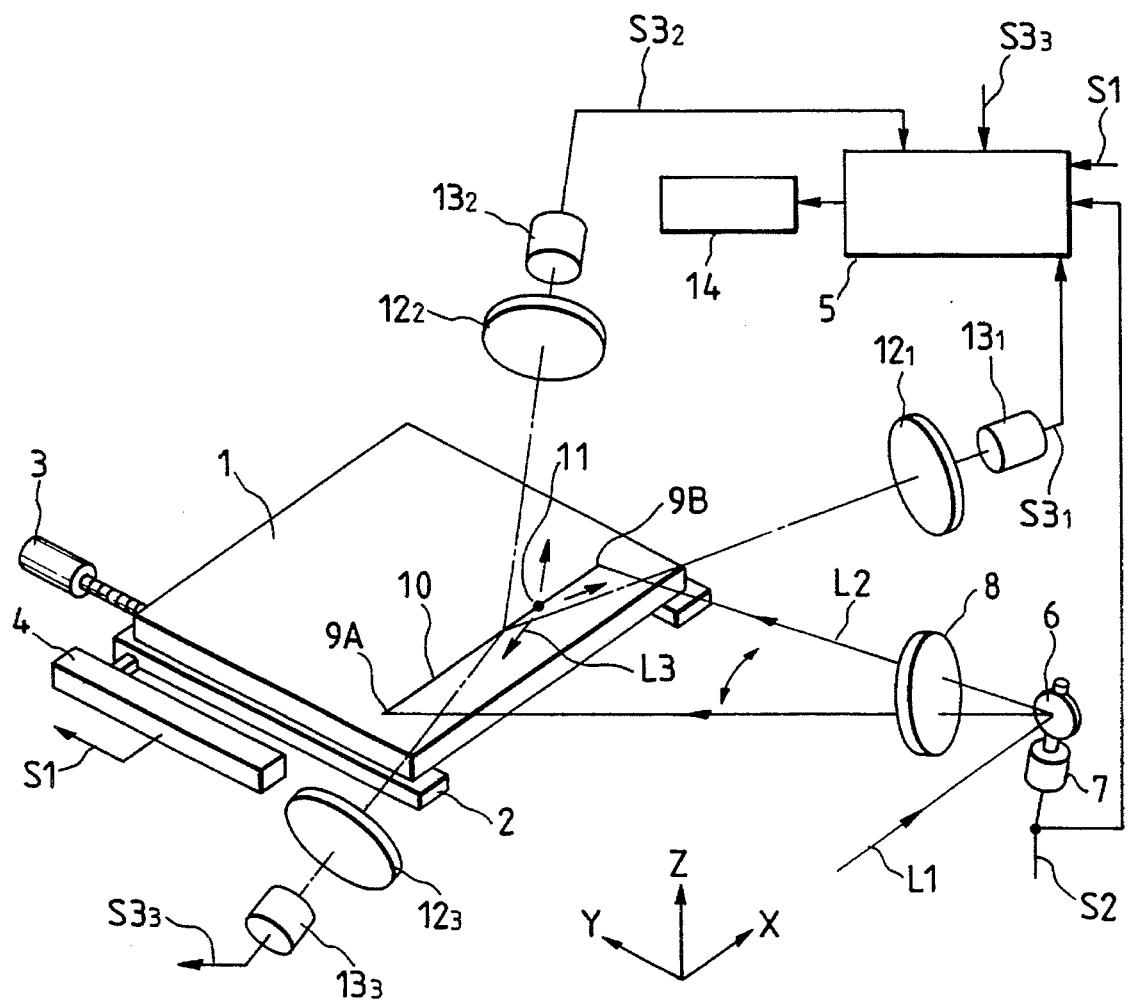
FIG. 16 is a perspective view of a conventional foreign particle inspection apparatus.

The configuration in FIG. 14 is modified to that in FIG. 15, when the non-telecentric scanning method is adopted. In FIG. 15, the scanning line 22 is illuminated in a non-telecentric state, and the central two light-receiving systems consisting of the imaging lenses 24C, 24D and the photodetectors 25C, 25D have optical axes which are mutually parallel and perpendicular to the scanning line 22. The first two light-receiving systems positioned outside and consisting of the imaging lenses 24B, 24E and the photodetectors 25B, 25E have optical axes inclined by an angle $\Theta_4$ to the line perpendicular to the scanning line 22, and the two light-receiving systems positioned further outside and consisting of the imaging lenses 24A, 24F and the photodetectors 25A, 25F have optical axes inclined by an angle $\Theta_3$ ($>\Theta_4$) to the normal line to the scanning line 22. In this case the angles $\Theta_3$ and $\Theta_4$ may be so selected as to satisfy a relation $\Theta_3 \leq \Theta_4$ or $\Theta_4 \leq \Theta_3$ so as to achieve light reception and signal processing in optimum manner.

The present invention is naturally not limited to the foregoing embodiments but is subject to modifications within the scope and spirit of the appended claims.

What is claimed is:

1. A foreign particle inspection apparatus, comprising:

an illuminating system for irradiating an inspection area on a specimen with inspecting light;

plural light-receiving systems adapted to condense scattered light generated by a foreign particle in said inspection area irradiated with said inspecting light, said light-receiving systems having respective light-receiving areas on said specimen, each smaller than said inspection area, wherein each of the light-receiving areas of said plural light-receiving systems overlaps partially with at least one of the other light-receiving areas, and said plural light-receiving systems are so arranged that every point in said inspection area is positioned in an overlapping region of a plurality of said light-receiving areas; and a foreign particle detection system for detecting the foreign particle in said inspection area, based on outputs of said plural light-receiving systems, wherein said foreign particle detection system is adapted to identify a presence of a foreign particle in said overlapping region only when scattered light exceeding a predetermined level is received by the light-receiving systems corresponding to all of the plurality of light-receiving areas overlapped in said overlapping region.

2. A foreign particle inspection apparatus according to claim 1, further comprising filters, provided respectively at the pupil planes of said plural light-receiving systems, for distinguishing between diffracted light from a periodic pattern formed on said specimen and the scattered light from a foreign particle.

3. A foreign particle inspection apparatus according to claim 1, wherein said illuminating system includes a telecentric optical system for attaining a uniform illuminating condition in the entire inspection area.

4. A foreign particle inspection apparatus, comprising:

an illuminating system for irradiating an inspection area, extending in line shape in a predetermined direction on a specimen, with inspecting light;

plural light-receiving systems adapted to condense scattered light generated by a foreign particle in said inspection area irradiated with said inspecting light, said light-receiving systems having respective light-receiving areas on said specimen, each having a dimension in said predetermined direction smaller than that of said inspection area in said predetermined direction, wherein said plural light-receiving systems are so arranged that each of the light-receiving areas thereof overlaps partially with the light-receiving area of an adjacent light-receiving system in said predetermined direction and that every point in said inspection area is positioned in an overlapping region of a plurality of said light-receiving areas; and a foreign particle detection system for detecting the foreign particle in said inspection area, based on outputs of said plural light-receiving systems, wherein said foreign particle detection system is adapted to identify a presence of a foreign particle in said overlapping region only when scattered light exceeding a predetermined level is received by the light-receiving systems corresponding to all of the plurality of light-receiving areas overlapped in said overlapping region.

5. A foreign particle inspection apparatus according to claim 4, wherein the light-receiving areas of mutually adjacent light-receiving systems overlap by $((n-1)/n)x$, where x is a dimension of the light-receiving areas of said mutually adjacent light-receiving systems in said predetermined direction, and n is an integer equal to at least 2.

6. A foreign particle inspection apparatus according to claim 5, wherein said foreign particle detection system includes plural photoelectric converters for photoelectrically converting lights respectively condensed by said plural light-receiving systems so as to output photoelectric converted signals, and n signal processing systems for processing the photoelectric converted signals from respective groups of photoelectric converters, wherein each group is composed of photoelectric converters corresponding to a respective set of light-receiving areas, each set of light-receiving areas being constituted by including in said set every n-th light-receiving area in sequence in said predetermined direction.

7. A foreign particle inspection apparatus according to claim 6, wherein said foreign particle detection system is adapted to identify the presence of a foreign particle when signals indicating the foreign particle are obtained from all of said n signal processing systems.

8. A foreign particle inspection apparatus according to claim 5, wherein said foreign particle detection system includes an optical fiber for guiding, to an exit end thereof, lights condensed by a group of light-receiving systems corresponding to a set of light-receiving areas constituted by including in said set every n-th light-receiving area in sequence in said predetermined direction, and photoelectric conversion means for receiving light output from said optical fiber.

9. A foreign particle inspection apparatus according to claim 4, further comprising filters, provided respectively at the pupil planes of said plural light-receiving systems, for intercepting the diffracted light from a periodic pattern formed on said specimen.

10. A foreign particle inspection apparatus according to claim 4, wherein said illuminating system includes a telecentric optical system for attaining a uniform illuminating condition in the entire inspection area.

11. A foreign particle inspection apparatus, comprising:

an illuminating system for irradiating an inspection area on a specimen with inspecting light;

plural light-receiving systems adapted to condense scattered light generated by a foreign particle in said inspection area irradiated with said inspecting light, said light-receiving systems having respective light-receiving areas on said specimen, each smaller than said inspection area, wherein each of the light-receiving areas of said plural light-receiving systems overlaps partially with at least one of the other light-receiving areas, and overlapped portions of the light-receiving areas of said plural light-receiving systems form a substantially continuous succession of partial inspection areas such that substantially every point in said inspection area is positioned in one of said partial inspection areas formed by said overlapped portions; and a foreign particle detection system for detecting the foreign particle in said inspection area based on outputs of said plural light-receiving systems.

12. A foreign particle inspection apparatus according to claim 11, wherein said foreign particle detection system is adapted to identify a presence of a foreign particle in one of said partial inspection areas only when scattered light exceeding a predetermined level is received by all of the light-receiving systems corresponding to that partial inspection area.

13. A foreign particle inspection apparatus according to claim 11, further comprising filters, provided respectively at the pupil planes of said plural light-receiving systems, for distinguishing between diffracted light from a periodic pattern formed on said specimen and the scattered light from a foreign particle.

14. A foreign particle inspection apparatus according to claim 11, wherein said illuminating system includes a telecentric optical system for attaining a uniform illuminating condition in the entire inspection area.

15. A foreign particle inspection apparatus, comprising:

an illuminating system for irradiating an inspection area, extending in line shape in a predetermined direction on a specimen, with inspecting light;

plural light-receiving systems adapted to condense scattered light generated by a foreign particle in said inspection area irradiated with said inspecting light, said light-receiving systems having respective light-receiving areas on said specimen, each having a dimension in said predetermined direction smaller than that of said inspection area in said predetermined direction, wherein said plural light-receiving systems are so arranged that each of the light-receiving areas thereof overlaps partially with the light-receiving area of an adjacent light-receiving system in said predetermined direction and overlapped portions of the light-receiving areas of said plural light-receiving systems form a substantially continuous succession of partial inspection areas, such that substantially every point in said inspection area is positioned in one of said partial inspection areas; and a foreign particle detection system for detecting the foreign particle in said inspection area, based on outputs of said plural light-receiving systems.

16. A foreign particle inspection apparatus according to claim 15, wherein said foreign particle detection system is adapted to identify a presence of a foreign particle in one of said partial inspection areas only when scattered light exceeding a predetermined level is received by all of the light-receiving systems corresponding to that partial inspection area.

17. A foreign particle inspection apparatus according to claim 15, wherein the light-receiving areas of mutually adjacent light-receiving systems overlap by $((n-1)/n)x$, where x is a dimension of the light-receiving areas of said mutually adjacent light-receiving systems in said predetermined direction, and n is an integer equal to at least 2.

18. A foreign particle inspection apparatus according to claim 17, wherein said foreign particle detection system includes plural photoelectric converters for photoelectrically converting lights respectively condensed by said plural light-receiving systems so as to output photoelectric converted signals, and n signal processing systems for processing the photoelectric converted signals from respective groups of photoelectric converters, wherein each group is composed of photoelectric converters corresponding to a respective set of light-receiving areas, each set of light-receiving areas being constituted by including in said set every n-th light-receiving area in sequence in said predetermined direction.

19. A foreign particle inspection apparatus according to claim 18, wherein said foreign particle detection system is adapted to identify the presence of a foreign particle when signals indicating the foreign particle are obtained from all of said n signal processing systems.

20. A foreign particle inspection apparatus according to claim 17, wherein said foreign particle detection system includes an optical fiber for guiding, to an exit end thereof, lights condensed by a group of light-receiving systems corresponding to a set of light-receiving areas constituted by including in said set every n-th light-receiving area in sequence in said predetermined direction, and photoelectric conversion means for receiving light output from said optical fiber.

21. A foreign particle inspection apparatus according to claim 15, further comprising filters, provided respectively at the pupil planes of said plural light-receiving systems, for intercepting the diffracted light from a periodic pattern formed on said specimen.

22. A foreign particle inspection apparatus according to claim 15, wherein said illuminating system includes a telecentric optical system for attaining a uniform illuminating condition in the entire inspection area.

* * * * *